US00PP16076P2

(12) United States Plant Patent
Egger

(10) Patent No.: US PP16,076 P2
(45) Date of Patent: Oct. 25, 2005

(54) ***HEUCHERA* PLANT NAMED 'STARRY NIGHT'**

(50) Latin Name: *Heuchera hybrida*
Varietal Denomination: Starry Night

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 78 days.

(21) Appl. No.: 10/942,362

(22) Filed: Sep. 15, 2004

(51) Int. Cl.[7] ..... A01H 5/00
(52) U.S. Cl. ..... Plt./263
(58) Field of Search ..... Plt./263

*Primary Examiner*—Anne Marie Grunberg
(74) *Attorney, Agent, or Firm*—Klarquist Sparkman, LLP

(57) ABSTRACT

A new and distinct hybrid of *Heuchera* plant characterized by very dark leaves throughout the year, a compact habit, and bicolor pink and white flowers.

1 Drawing Sheet

Botanical classification: *Heuchera hybrida.*
Variety designation: 'Starry Night'.

The present invention relates to a new and distinct cultivar of *Heuchera* hybrid and given the cultivar name of 'Starry Night'. *Heuchera* is in the family Saxifragaceae. *Heuchera* 'Starry Night' originated from a cross between H-01-dklf-11 (an unpatented, proprietary plant) as the seed parent and a white *Heuchera sanguinea* (unpatented), as the male parent. Given its very dark leaves, we know that the seed parent, H-01-dklf-11, has *Heuchera americana* in its parentage.

This new *Heuchera* is distinguished by:

1. Medium size, dark leaves with a matte finish.
2. Dark flower stems with numerous flowers.
3. Pink buds to bicolor pink and white flowers.
4. Compact habit.
5. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows a one-year-old *Heuchera* 'Starry Night' growing in a one-gallon pot in Canby, Oreg.

DETAILED PLANT DESCRIPTION

The following is a detailed description of the new *Heuchera* cultivar based on observations of a one-year-old specimen grown in a one-gallon container in Canby, Oreg. The color descriptions are all based on The Royal Horticultural Society Colour Chart.

Botanical classification: *Heuchera* hybrid.
Variety designation: 'Starry Night'.

Plant:
- *Form.*—Basal rosette, herbaceous perennial.
- *Hardiness.*—USDA Zone 4 to 9.
- *Size.*—18 cm tall and 38 cm wide.
- *Habit.*—Compact, rounded.

Leaf:
- *Type.*—Simple.
- *Arrangement.*—Rosette.
- *Shape.*—Broadly ovate.
- *Lobing/division.*—5 to 7 shallow rounded lobes, with 1 to 2 Shallow secondary lobes.
- *Venation.*—Palmate.
- *Margins.*—Crenate. At sinuses, lobes are often slightly raised up and pinched in.
- *Apex.*—Obtuse.
- *Base.*—Cordate.
- *Blade size.*—5.5 to 8.5 cm long and 6 to 9.5 cm wide.
- *Vestiture.*—Glandular.
- *Aspect.*—Matte.
- *Texture.*—Leathery.
- *Petiole length.*—8 to 9 cm.
- *Petiole vestiture.*—Glandular.
- *Petiole color.*—Greyed Orange 166A to Brown 200C.
- *Leaf color.*—Summer abaxial — Purpled brown, between Greyed Purple 187A and Brown 200A. Spring abaxial — Between Brown 200A and Green 147A with a slight veil, Greyed Green 196A. Adaxial, spring and summer — Closest to Greyed Purple 187A but grayer.

Inflorescence:
- *Type.*—Thyrse.
- *Number of flowers.*—100 to 200 per thyrse.
- *Size.*—20 to 37 cm long and 8 to 15 cm wide.
- *Peduncle.*—With 0 to 2 petiolate, small, cauline leaves, ovate, with jagged margins, which curl back. Height — 65 cm. Diameter — 0.4 cm near base. Color — Dark maroon, Greyed Purple 187A. Vestiture — Glandular.
- *Pedicel.*—Length — 0.2 cm. Vestiture — Glandular. Color — Greyed Purple 187A.
- *Bloom period.*—May through July in Canby, Oreg.

Flower bud:
- *Size.*—0.3 cm wide and 0.7 cm long.
- *Description.*—Oblong.

*Vestiture.*—Heavily glandular.
*Color.*—Red Purple 58A on bottom half and main vein of top half with Yellow White 158C on top half.

Flower:
*Type.*—Perfect, zygomorphic, sepals are petaloid.
*Shape.*—Campanulate.
*Size.*—0.9 cm long and 0.6 cm wide.
*Petal count.*—5, inconspicuous.
*Petal color.*—White 155D.
*Petal shape.*—Spatulate with a clawed base.
*Petal size.*—0.3 cm long.
*Calyx.*—Showy with 5 lobes, divided ½ way to the base, heavily glandular outside.
*Calyx size.*—0.6 cm long and 0.65 cm wide.
*Calyx and flower color.*—Outside: White 155C on the top half with a pink base, Red Purple 58A. Inside: White 155C. Fade to Yellow Green 150.
*Stamen number.*—5.
*Pistil length.*—0.6 cm.
*Pistil color.*—White 155A with a red purple stigma, Red Purple 58A.
*Pollen color.*—No pollen, male sterile.
*Fragrance.*—None.
*Lastingness.*—Each thryse blooms for about 4 weeks on the plant.

Fruit:
*Type.*—Two-beaked ovoid capsule.
*Fertility.*—Fertile.
*Color.*—Brown 200D.

Seed:
*Shape.*—Linear.
*Size.*—2 mm long.
*Color.*—Black. RHS 202A.

Disease and pest tolerance: *Heuchera* 'Starry Night' shows excellent disease resistance to powdery mildew, the common problem of *Heuchera*. All *Heuchera* are susceptible to root weevils.

COMPARISON TO SIMILAR *HEUCHERAS*

Compared to *Heuchera* 'Champagne Bubbles' (U.S. Plant Pat. No. 11,259), *Heuchera* 'Starry Night' has dark foliage rather than green and whiter flowers.

Compared to *Heuchera* 'Ebony and Ivory' (U.S. Plant Pat. No. 11,380), *Heuchera* 'Starry Night' has taller flower stems, larger, pinker flowers, less wavy leaf margins, and darker summer foliage.

Compared to *Heuchera* 'Obsidian' (U.S. Plant Pat. No. 14,836), *Heuchera* 'Starry Night' has leaves that are lighter and has flowers that are much larger, showier, and bicolor pink and white.

I claim:

1. A new and distinct hybrid of *Heuchera* plant characterized by very dark leaves throughout the year, a compact habit, and bicolor pink and white flowers.

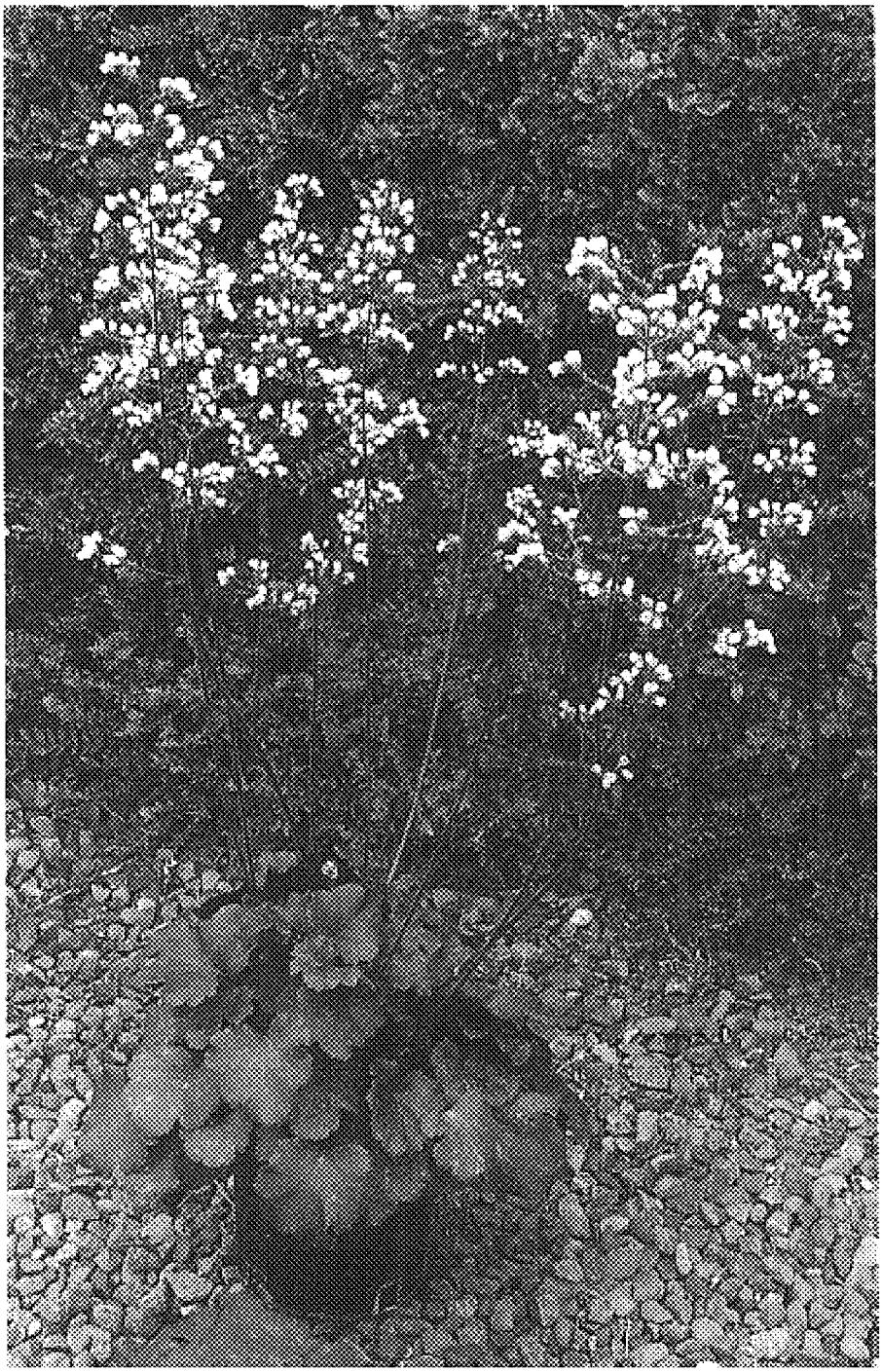

* * * * *